United States Patent [19]

Ahn

[11] Patent Number: 5,571,117
[45] Date of Patent: Nov. 5, 1996

[54] METHOD OF ENDOSCOPIC STAPLING AND SUTURING AND INSTRUMENT THEREFOR

[75] Inventor: Young W. Ahn, Marietta, Ga.

[73] Assignee: Emory University, Atlanta, Ga.

[21] Appl. No.: 398,995

[22] Filed: Mar. 6, 1995

[51] Int. Cl.$^6$ .................................................. A61B 17/04
[52] U.S. Cl. ............................................. 606/139; 227/19
[58] Field of Search ..................................... 227/175–180, 227/19; 606/139, 143, 144

[56] References Cited

U.S. PATENT DOCUMENTS

| | | |
|---|---|---|
| 4,378,901 | 4/1983 | Akopov et al. . |
| 4,749,114 | 6/1988 | Green ......................................... 227/19 |
| 4,821,939 | 4/1989 | Green ......................................... 227/19 |
| 5,037,021 | 8/1991 | Mills et al. . |
| 5,040,715 | 8/1991 | Green et al. . |
| 5,242,457 | 9/1993 | Akopov et al. . |
| 5,257,713 | 11/1993 | Green et al. . |
| 5,289,963 | 3/1994 | McGarry et al. . |
| 5,333,772 | 8/1994 | Rothfuss et al. .......................... 227/19 |
| 5,368,599 | 11/1994 | Hirsch et al. ............................ 227/175 |

OTHER PUBLICATIONS

Cornella, et al., *Ob and Gyn.*, 45(12):805–816, 1990.
Cutner, et al., *The Practitioner*, 235:98–104, Feb. 1991.
Stuart L. Stanton, *Clinical Ob. and Gyn.*, 33(2):346–357, Jun. 1990.

Davis and Lobel, "Laproscopic Urothropexy for the Correction of Stress Urinary Incontinence and Cystocele:Evolution of Technique and Results of a Pilot Study" Abstract No. 20, p. 391, 1993.

*Primary Examiner*—Gary Jackson
*Attorney, Agent, or Firm*—Needle & Rosenberg, P.C.

[57] ABSTRACT

An endoscopic surgical stapler and suture placing instrument is provided having a means adjacent the distal end for removably positioning a suture in front of and in registry with the staple discharge opening such that a staple discharged therefrom will affix the suture to a target tissue. An apparatus for adapting an existing endoscopic stapler is also provided wherein the apparatus comprises a means for positioning a suture in front of and in registry with the staple discharge opening. A method of suturing a target tissue of an individual by suturing the target tissue with the novel endoscopic surgical stapler and suture placing instrument is also provided. The invention provides that this method is particularly well-adapted to an individual undergoing a modified Burch's procedure for stress urinary incontinence or a presacral corpopexy procedure for vaginal prolapse.

13 Claims, 5 Drawing Sheets

METHOD OF ENDOSCOPIC STAPLING AND SUTURING AND INSTRUMENT THEREFOR

FIELD OF THE INVENTION

The present invention relates to the field of endoscopic surgical instruments. In particular, the invention relates to the field of improved stapling and suturing through endoscopy.

BACKGROUND OF THE INVENTION

As medical technology advances, surgical procedures are increasingly being achieved through endoscopy. The main advantages of using endoscopy for various types of surgery is that the minimally invasive endoscope decreases surgical operating time and reduces post-operative complications, such as bacterial infection. This, in turn, reduces the patient's discomfort, recovery time and hospital stay. In particular, elderly patients who are vulnerable to the risks associated with prolonged general anesthesia and healing from major surgery benefit from endoscopic modifications of traditional surgical procedures.

An example of a surgical procedure which has been improved by endoscopy is the procedure to correct stress urinary incontinence in females. In stress urinary incontinence, the patient leaks urine in response to a sudden increase in the intra-abdominal pressure secondary to such acts as coughing, sneezing, laughing, and lifting. Problems with connective tissue support of the proximal urethra and vesical neck are by far the most common causes of stress incontinence. See, DeLancey, "Anatomy and Physiology of Urinary Continence," *Clin. Ob. & Gyn.*, 33(2): 298–307 (1990). In the average woman in the supine position, the urethral pressure ranges from 40 to 80 cm $H_2O$ and the intra-abdominal pressure from 5 to 10 cm $H_2O$. During coughing or stress maneuvers, there is an increase of 20 to 100 cm $H_2O$ in abdominal and bladder pressures. However, urinary incontinence does not occur in normal women for three reasons. First, a reflex contraction of the pelvic floor muscles increases urethral pressure. Second, the normal female urethra is in a well-supported retropubic position; therefore, any increase in pressure is transmitted to the bladder, urethra, and bladder neck, thus maintaining the pressure gradient. Third, the locus of force generated is experienced, not at the bladder neck (located in a non-dependent position), but at the bladder base, which is the most dependent structure. See, Snyder and Lipsitz, "Evaluation of Female Urinary Incontinence," *Urological Clinics of N. Amer.*, 18(2): 197–209 (1991).

A modified Burch's procedure, or Marshall-Marchetti-Krantz operation, attempts to alleviate stress urinary incontinence in females by resecuring the urethra in its normal retropubic position. This procedure generally requires placement of sutures between the paraurethral tissues of the anterior vaginal mucosa and the periosteum of the pubic bone. Either one or two (but sometimes three or more) pairs of sutures are placed, depending upon the particular case and the preference of the surgeon. A final one or two sutures are taken to fix the anterior aspect of the bladder to the superior aspect of the symphysis. This suture is passed from Cooper's ligament on the one side, into the bladder wall at the midline, and to the Cooper's ligament on the other side. This successfully suspends the bladder neck to relieve gravitational tension thereon. See, Ridley, "Technique of the Marshall-Marchetti-Krantz Operation," in *Gynecological Surgery: Errors, Safeguards, Salvage*, 2nd Ed., pp. 194–197 (1981).

The fact that different variations of these surgical procedures have been developed for the treatment of stress incontinence reflects the current lack of complete success in the field. See, Fischer-Rasmussen, "Treatment of Stress Urinary Incontinence," *Ann. Med.*, 22:455–465 (1990). Due to the apparent advantages of endoscopy, the modified Burch's procedure for the correction of stress urinary incontinence has been adapted for the endoscopic delivery of the necessary sutures. See, Stanton, "Surgical Management of Urethral Sphincter Incompetence," *Clin. Ob & Gyn.*, 33(2): 346–357 (1990).

Presacral corpopexy for the correction of vaginal prolapse similarly requires the placement of sutures in the apex of the vaginal cavity to approximate pre-sacral ligaments. When presacral corpopexy is performed via conventional surgical techniques, a very large abdominal incision is required to reach the presacral ligament. See, Romney et at., "Disorders of Pelvic Support" in *Gynecology and Obstetrics, The Health Care of Women*, pp.974–977 (1981). Therefore, this procedure has also been adapted for endoscopic surgery with some success.

The risks of traditional surgery have been partially reduced through the adaptation of endoscopy to these and other procedures, however, the currently employed practices require the insertion of two separate surgical tools in addition to the endoscope for conventional needle placement and securing of sutures in the appropriate tissue. Thus, the current endoscopic tools and procedures require making an unnecessary additional incision in the patient, and require the assistance of a second surgeon or surgical assistant during the procedure to aid in suture placement.

Furthermore, current endoscopes and procedures require a series of unnecessary movements within the surgical site to secure and manipulate sutures during placement, which increases tissue trauma and the chances of surgical errors occurring. This is especially true when the procedure is performed on very delicate tissues and in a confined space, such as in a modified Burch's procedure for stress urinary incontinence or a presacral corpopexy procedure for vaginal prolapse, as described above.

Advances toward reducing the surgical risk associated with endoscopic repair of stress urinary incontinence have focused on improved needle design for use with endoscopic needle drivers. The Stamey-type needle is a preferred needle for use in endoscopic repair of stress urinary incontinence. See, Davis and Lobel, "Laparoscopic Urothropexy For The Correction Of Stress Urinary Incontinence And Cystocele: Evolution Of Technique And Results Of A Pilot Study" (1993). Endoscopic suture placement with a needle, however, still requires additional time, manpower and trauma. Thus, there is a need in the an to provide a single endoscopic surgical device which provides rapid effective securing of sutures at a desired location.

OBJECTS OF THE INVENTION

Therefore, it is an object of the present invention to provide a single endoscopic surgical device which provides rapid effective securing of sutures at a desired location.

It is a further object of the invention to provide an endoscopic surgical instrument which permits the selective stapling of sutures to tissues.

It is a further object of the invention to provide an endoscopic surgical instrument which has a means for removably positioning a suture in from of and in registry with the staple discharge opening.

It is a further object of the invention to provide an endoscopic surgical instrument which has a means for selectively securing the sutures to the instrument.

It is a further object of the invention to provide an apparatus adapted for attachment to the distal end an endoscopic surgical stapling instrument which provides a means for removably positioning a suture in from of and in registry with the staple discharge opening such that a staple discharged therefrom will affix the suture to a target tissue.

It is a further object of the invention to provide a method of performing an endoscopic surgical procedure with the instrument of the invention.

A further object of the invention is to provide a method of endoscopic suture placement utilizing the instrument of the invention.

Another object of the invention is to provide an improved method of endoscopic surgical repair of stress urinary incontinence comprising utilizing staple affixation of a suture to tissue at a desired location.

A further object of the invention is to provide a method of endoscopic suture placement at a predetermined site comprising affixing a suture to a target tissue with a staple wherein the staple and suture are delivered to the predetermined site by the same instrument.

SUMMARY OF THE INVENTION

The present invention provides an endoscopic surgical stapler and suture placing instrument having a proximal end, an opposite distal end, and a body portion housing a stapling mechanism having an opening at the distal end of said body portion for discharging a staple therefrom The endoscopic surgical stapler and suture placing instrument has a means adjacent the distal end for removably positioning a suture in front of and in registry with the staple discharge opening such that a staple discharged therefrom will affix the suture to a target tissue.

The invention also provides an apparatus adapted for positioning on an existing endoscopic surgical stapling instrument of the type having a proximal end, an opposite distal end, and a body portion housing a stapling mechanism having an opening at the distal end of said body portion for discharging a staple therefrom, wherein the apparatus comprises a means for removably positioning a suture in front of and in registry with the staple discharge opening, such that a staple discharged therefrom will affix the suture to a target tissue.

The invention also provides a method of suturing a target tissue of an individual comprising suturing the target tissue with the novel endoscopic surgical stapler and suture placing instrument. The invention provides that this method is particularly well-adapted to an individual undergoing a modified Burch's procedure for stress urinary incontinence or a presacral corpopexy procedure for vaginal prolapse.

DETAILED DESCRIPTION OF THE INVENTION

Figure 1:
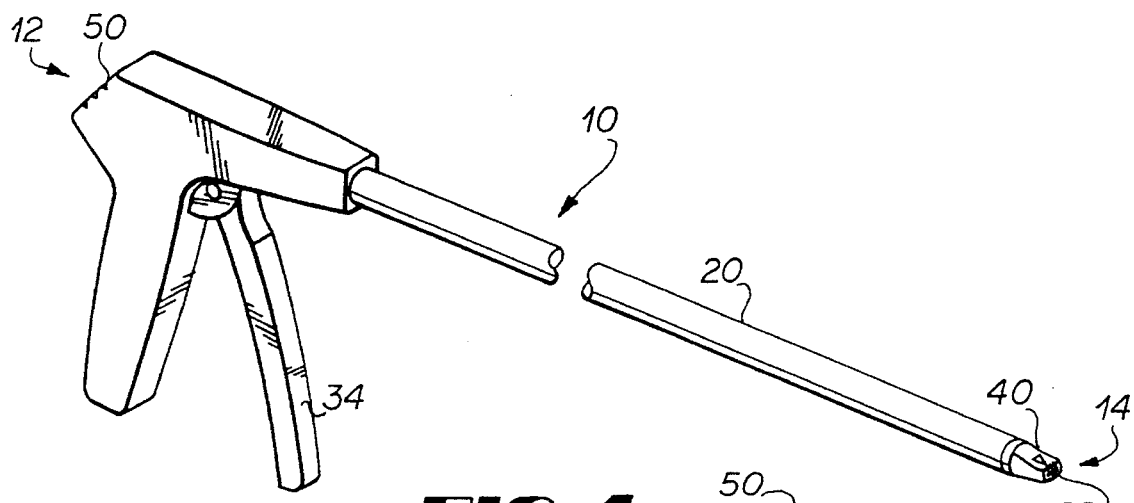
FIG. 1 is a perspective view of the endoscopic surgical stapler and suture placing instrument of the present invention.
Figure 2:
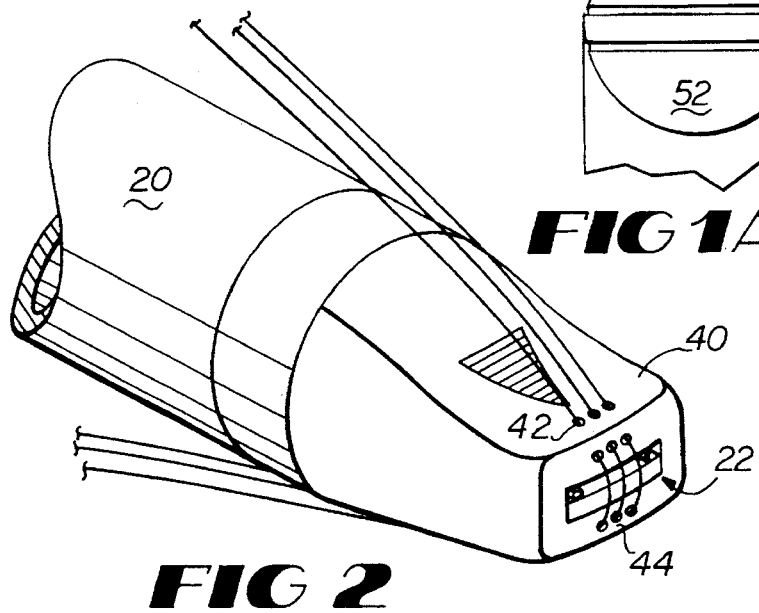
FIG. 2 is a detailed partial view of the distal end of the instrument disclosing the means for removably positioning a suture in from of and in registry with the staple discharge opening.
Figure 3:
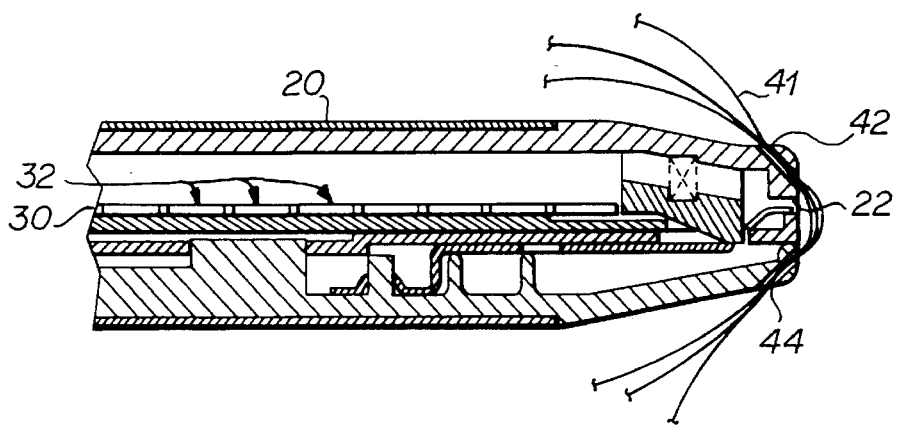
FIG. 3 is a vertical cross-sectional view of the distal end of the instrument taken along the longitudinal axis.

As seen in FIGS. 1–3, the endoscopic surgical stapler and suture placing instrument 10 has a proximal end 12, an opposite distal end 14, and a body portion 20 housing a stapling mechanism 30 having an opening 22 at the distal end 14 of said body portion 20 for discharging a staple 32 therefrom. The endoscopic surgical stapler and suture placing instrument 10 has a means 40 adjacent the distal end 14 for removably positioning a suture 41 in front of and in registry with the staple discharge opening 22 such that a staple 32 discharged therefrom will affix the suture 41 to a target tissue 60 (see FIG. 4). The invention contemplates that the suture positioning means may be provided in the form of a groove, slot, eyelet, hole, or other suture guide located adjacent to the staple discharge opening 22.

As shown in FIGS. 1 and 3 the stapling mechanism 30 can be of a type commonly known in the art. The trigger 34 is used for firing the staples 32. The trigger 34 is connected to a driving means (not shown) which pushes the staples 32 forward and individually out the opening 22 with a force sufficient to penetrate all potential target tissues, including bone. Thus, the trigger 34 controls the incremental advancement of staples 32, which are usually loaded in a magazine type cartridge. A typical stapling endoscope of this type can be seen in Rothfuss et at. "Multiple Fire Endoscopic Stapling Mechanism" European Patent Application Publication No. 536,903 A2 or U.S. Pat. No. 5,289,963 issued to McGarry et al.

As seen in FIG. 4, the instrument 10 is intended to be used for the repair or joining of tissues 60. In FIG. 4A, the body portion 20 of the instrument 10 is positioned at the site of the tissues 60 to be repaired. This may be achieved with the aid of a trocar cannula or tube (not shown), designed for the insertion of endoscopes into the body. In FIGS. 4A–4E the target tissue 60 is shown exposed to provide a better view of the procedure. In FIG. 4B the positioning means 40 of the instrument 10 is placed against a first tissue surface 62 where a staple 32 is discharged. The portion of the sutures 41 which were in front of the staple discharge opening 22 thereby becoming affixed to the tissue 62. In FIG. 4C, the instrument 10 is shown having placed another staple 32 in the second tissue surface 64. The resulting configuration then permits joining the tissues 62, 64 with a purse suture as shown in FIG. 4E. This is achieved by drawing the excess suture 41 length away from the target tissue 60 to bring the first and second surfaces 62, 64 into apposition.

Figure 1A:
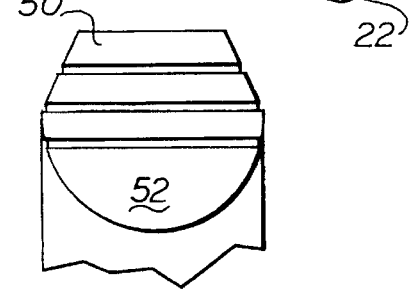
FIG. 1A is a detailed partial view of the proximal end of the instrument disclosing the means for temporarily retaining a suture.

As shown in FIGS. 1 and 1A, the instrument 10 is equipped with a means 50 adjacent the proximal end 12 for temporarily retaining the sutures 41 (shown in FIG. 2). This suture retaining means 50 is essentially a surface adapted with a textured thumb pad 52 for trapping and maintaining the tension on the sutures 41 while the tissues 62, 64 are drawn together by carefully withdrawing the distal end 14 of the instrument 10 from the target tissue 60 location. The invention contemplates a variety of suture retaining means 50 including, but not limited to, a suture grip, cleat, tie-down, or the like.

Following the stapling procedure, the sutures 41 are then removed from the instrument 10 and knotted. Knotting the sutures 41 is accomplished by the normal surgical procedure, including the use of a knot pusher (not shown) to deliver the knot through the trocar cannula to the tissue site. The sutures 41 may then be cut adjacent to the knot with endoscopic scissors, which are also inserted through the trocar cannula.

Figure 4A:
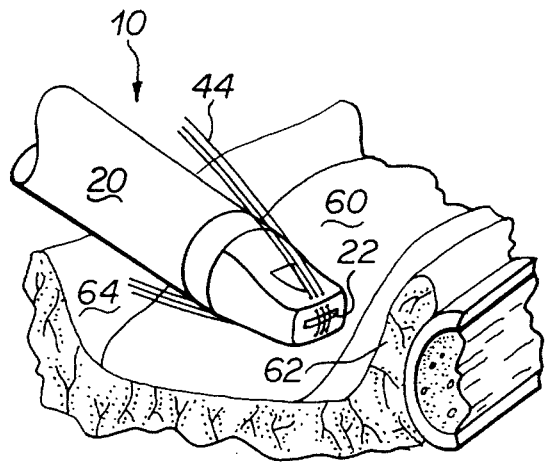
FIGS. 4A–4E show the endoscopic surgical stapler and suture placing instrument in use to repair a damaged tissue.
Figure 4B:
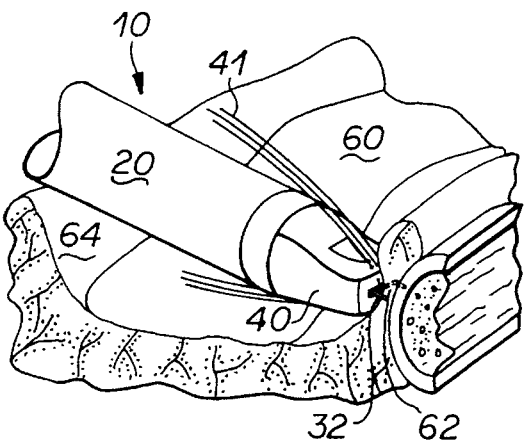
Figure 4C:
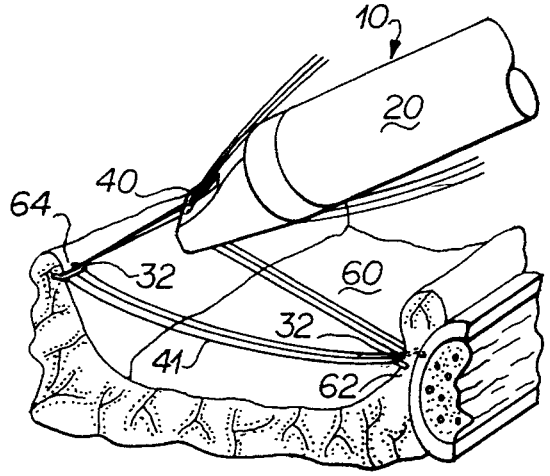
Figure 4E:
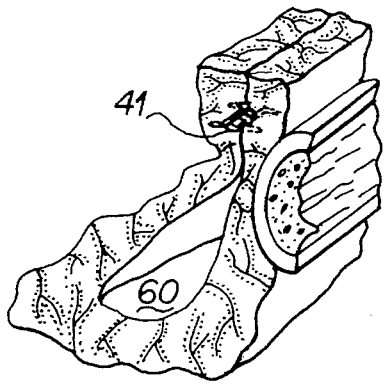
Figure 4D:
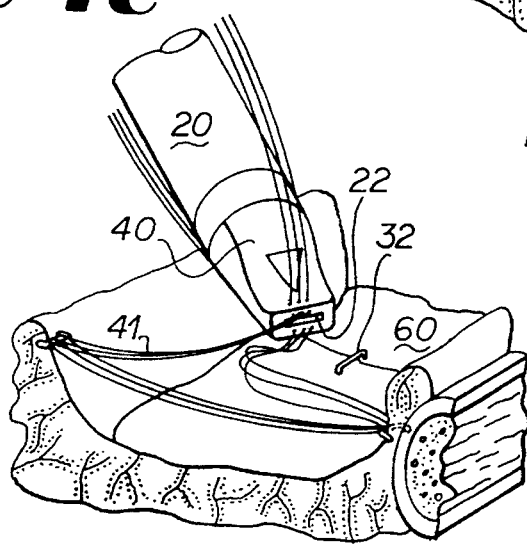

FIG. 4D shows that the instrument 10 is capable of placing a third staple 32 in tissue surface 60 which does not affix a suture 41 thereto. This unique feature permits the surgeon to perform collateral repairs of damaged tissues 60 directly with a staple 32 without having to change the instrument 10. This optional feature is achieved by simply ejecting a staple 32 when there is no suture 41 at the staple discharge opening 22. This can occur as a result of the above-described purse-string suture configuration as shown in FIGS. 4C and 4D. The surgeon may also elect to place a staple 32 without a suture 41 at any time at a desired location by releasing the suture 41 tension enough to permit the sutures 41 to temporarily slide away from, and out of registry with, the staple discharge opening 22. When necessary, the tissue area adjacent to site of the desired sutureless staple may be used to provide gentle resistance so as to permit sliding of the sutures 41 away from the staple discharge opening 22.

Referring to FIGS. 2 and 3 the instrument 10 further provides a positioning means 40 for the sutures 41 which has three pairs of complimentary suture guide holes 42, 44 disposed through the body portion 20 adjacent the distal end 14. The guide holes 42, 44 are located adjacent opposite sides of the staple discharge opening 22, thereby removably positioning the sutures 41 through the guide holes 42, 44 and in front of the staple discharge opening 22. These guide holes 42, 44, thus, serve to align the sutures 41 in front of the staple discharge opening 22 when tension is maintained on the sutures 41, and permit the sutures 41 to slide to either side of the staple discharge opening 22, and out of registry therewith, when the tension is released and the distal end 14 is moved. It is understood that the present invention contemplates an instrument which has one or more pairs of guide holes.

Figure 5:
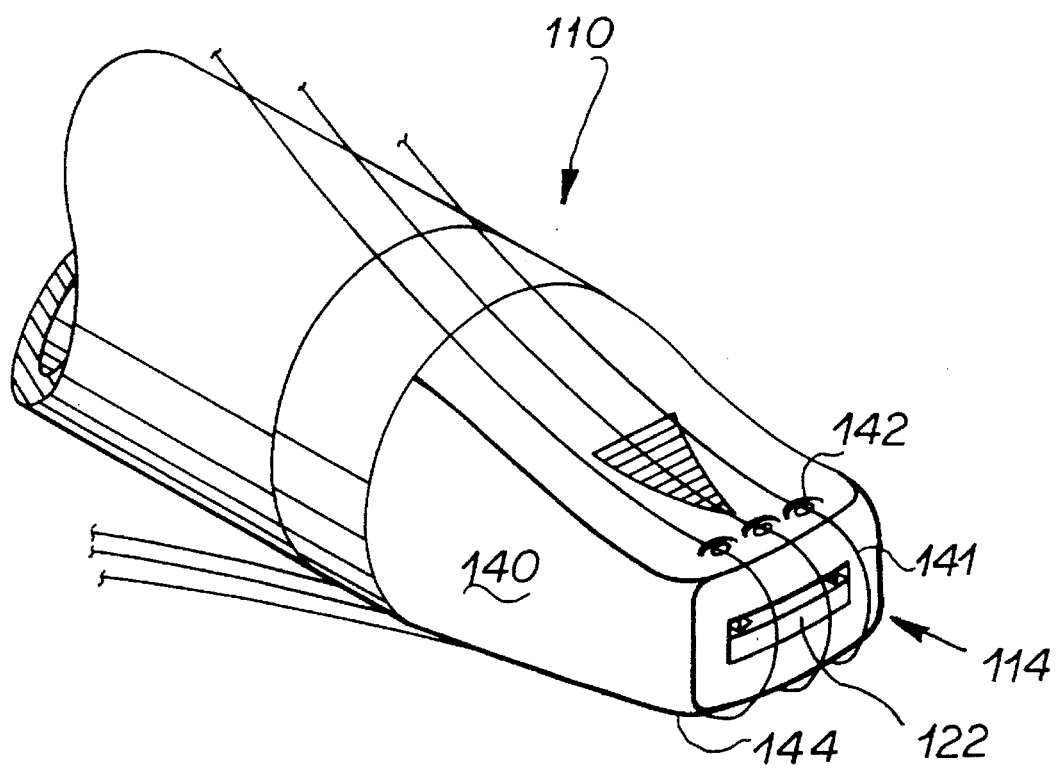
FIGS. 5 and 5A are detailed partial views of the distal end of the instrument disclosing alternate embodiments for the means for removably positioning a suture in from of and in registry with the staple discharge opening.

In another embodiment the invention shown in FIG. 5, the positioning means 140 comprises three pairs of complimentary suture guide eyelets 142, 144 adjacent the distal end 114 of the instrument 110. The eyelets 142, 144 are located adjacent opposite sides of the staple discharge opening 122, thereby removably positioning the sutures 141 through the guide eyelets 142, 144 and in front of and in registry with the staple discharge opening 122. It is understood that the present invention contemplates an instrument which has one or more pairs of guide eyelets. Additionally, the invention contemplates that a variety of suture positioning means may be used, including grooves, slots, holes, eyelets, or the like.

Figure 5A:
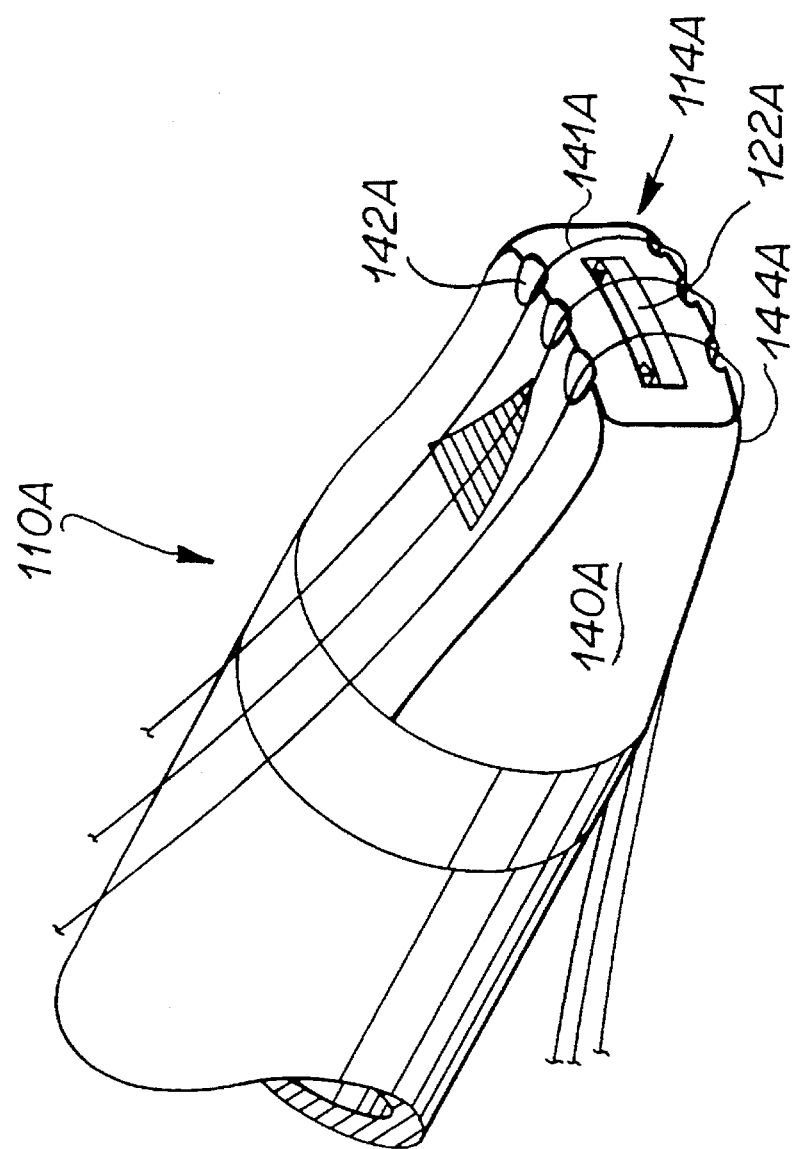

For example, FIG. 5A, shows an embodiment of the invention having a positioning means 140A provided in the form of three pairs of complimentary suture guide grooves 142A, 144A on the body portion adjacent the distal end 114A of the instrument 110A. The grooves 142A, 144A are located adjacent opposite sides of the staple discharge opening 122A, thereby removably positioning the sutures 141A through the guide grooves 142A, 144A and in front of and in registry with the staple discharge opening 122A.

Figure 6:
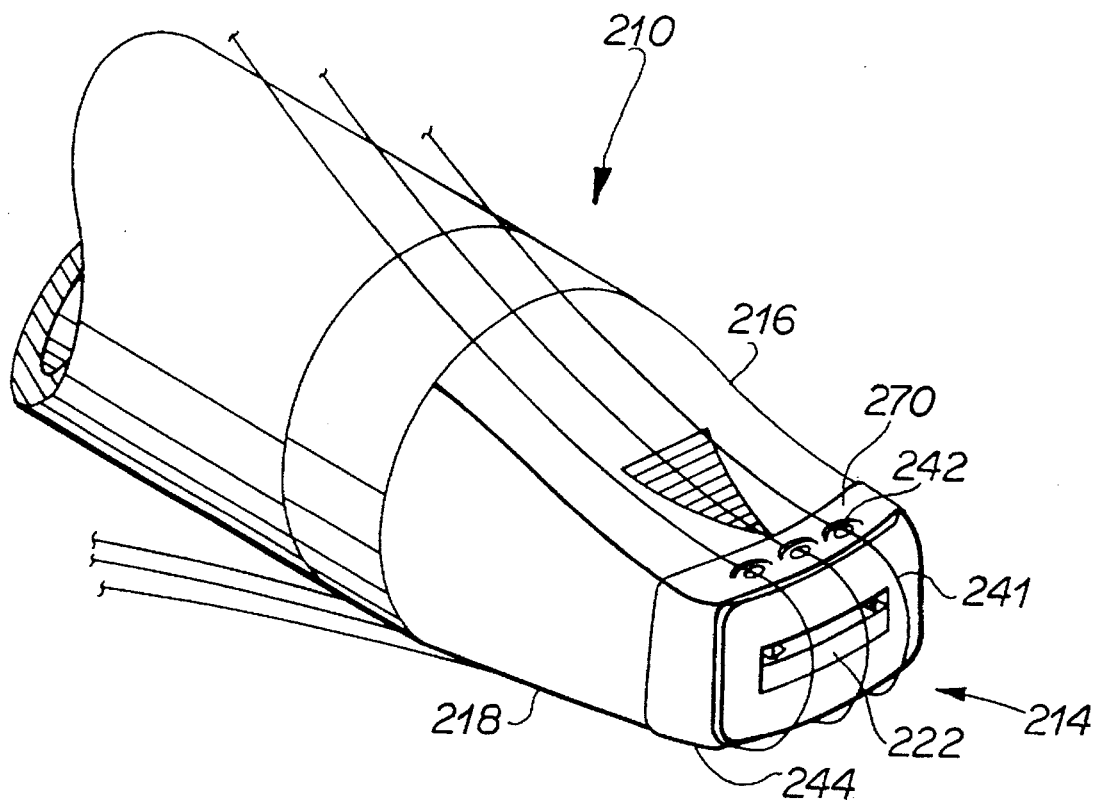
FIG. 6 is a detailed partial view of the distal end of an existing stapling instrument which has been adapted with an apparatus positioned on the distal end of the existing stapling instrument means for removably positioning a suture in front of and in registry with the staple discharge opening.

In the embodiment of the invention shown in FIG. 6, the invention provides an apparatus 270 adapted for positioning on an existing endoscopic surgical stapling instrument 210 of the type having a distal end 214 housing a stapling mechanism (not shown), having an opening 222 at the distal end 214 of said instrument 210 for discharging a staple (not shown) therefrom. The apparatus 270 is positioned on the distal end 214 of said instrument 210 and further comprises a means for removably positioning a suture 241 in front of and in registry with the staple discharge opening 222 such that a staple discharged therefrom will affix the suture 241 to a target tissue (not shown). In the embodiment shown in FIG. 6, the apparatus 270 is comprised of a ring-shaped element adapted to fit over and attach to the distal end 214 of instrument 210 such that staple discharge opening 222 is not obstructed. As shown, eyelets 242, 244 can provide the means for retaining suture 241 in proper position in front of the staple discharge opening 222. However, the invention contemplates that a variety of suture positioning means may be used, including grooves, slots, holes, eyelets, or the like. The apparatus 270 can be affixed to the endoscopic instrument 270 by any of several well-known means including, but not limited to adhesives, screws, and the like. Examples of existing models which can be so adapted include, but are not limited to, a multi-fire endohernia disposable surgical stapler (United States Surgical, Inc., Norwalk, Conn.) and an endosurgical stapler (Ethicon, Inc., Summerville, N.J.).

The invention also provides a method of suturing a target tissue 60 of an individual comprising suturing the target tissue 60 with the novel endoscopic surgical stapler and suture placing instrument 10 or 110, or adapted instrument 210. The invention provides that this method is particularly well-adapted to an individual undergoing a modified Burch's procedure for stress urinary incontinence or a presacral corpopexy procedure for vaginal prolapse.

In particular, the invention provides an improved method of endoscopic surgical repair of stress urinary incontinence comprising utilizing staple affixation of a suture to tissue at a desired location within the patient's body, for example as shown in FIGS. 4A–E. The method provides an improvement over current endoscopy procedures utilizing needle driven suture placement. Sutures 41 are affixed to a target tissue 62 by means of the endoscopic surgical stapling and suture placing instrument of the invention 10 or 110, or by use of the apparatus 270 adapted for positioning on an existing endoscopic surgical instrument 210 as shown in FIG. 6. It is contemplated by the invention that the method of endoscopic suture placement utilizing staple affixation of the suture to a target tissue can be utilized in any endoscopic surgical procedure where suture placement is required including, but not limited to, the specific examples provided herein.

A particular advantage of the methods of the invention is that the suture 41 and staple 32 used to affix the suture 41 to a target tissue 60 can be delivered to the target tissue 60 by the same instrument 10 as shown in FIGS. 4A–E. Accordingly, the invention provides a method of endoscopic suture placement at a predetermined site comprising affixing a suture 41 to a target tissue 60 with a staple 32 wherein the staple 32 and suture 41 are delivered to the predetermined site by the same instrument 10, 110 or 210. The predetermined site can be any site within the body where endoscopic procedures are performed and suture placement is desired.

As shown in FIG. 4, a single instrument 10 is used to simultaneously deliver the suture 41 and the staple 32 to the surgical site. Positioning means 40 retains the suture 41 in proper position such that the sutures 41 are overlying and in registry with the discharge opening 22.

As used in the claims, "a" means one or more than one, depending upon the context in which it is used and defined in the specification. These and other embodiments of the invention will be apparent to one skilled in the art.

What is claimed is:

1. An endoscopic surgical stapler and suture placing instrument having a proximal end, an opposite distal end, and a body portion housing a stapling mechanism having an opening at the distal end of said body portion for discharging a staple therefrom, comprising a means adjacent the distal end for removably positioning a suture in front of and in registry with the staple discharge opening such that a staple discharged therefrom will affix the suture to a target tissue.

2. The instrument of claim 1, further comprising a means adjacent the proximal end for temporarily retaining said suture.

3. A method of suturing a target tissue of an individual comprising suturing the target tissue with the endoscopic surgical stapler and suture placing instrument of claim 1.

4. The method of claim 3, wherein the individual is undergoing a modified Burch's procedure for stress urinary incontinence.

5. The method of claim 3, wherein the individual is undergoing a presacral corpopexy procedure for vaginal prolapse.

6. The instrument of claim 1, wherein the positioning means comprises a pair of complimentary suture guide grooves on the body portion adjacent the distal end, the grooves being located adjacent opposite sides of the staple discharge opening, thereby removably positioning the suture through the guide grooves and in front of and in registry with the staple discharge opening.

7. An endoscopic surgical stapler and suture placing instrument having a proximal end, an opposite distal end, and a body portion housing a stapling mechanism having an opening at the distal end of said body portion for discharging a staple therefrom, comprising a means adjacent the distal end for removably positioning a suture in front of and in registry with the staple discharge opening such that a staple discharged therefrom will affix the suture to a target tissue, wherein the positioning means comprises a pair of complimentary suture guide holes disposed through the body portion adjacent the distal end, the guide holes being located adjacent opposite sides of the staple discharge opening, thereby removably positioning the suture through the guide holes in front of and in registry with the staple discharge opening.

8. An endoscopic surgical stapler and suture placing instrument having a proximal end, an opposite distal end, and a body portion housing a stapling mechanism having an opening at the distal end of said body portion for discharging a staple therefrom, comprising a means adjacent the distal end for removably positioning a suture in front of and in registry with the staple discharge opening such that a staple discharged therefrom will affix the suture to a target tissue, wherein the positioning means comprises a pair of complimentary suture guide eyelets on the body portion adjacent the distal end, the eyelets being located adjacent opposite sides of the staple discharge opening, thereby removably positioning the suture through the guide eyelets and in front of and in registry with the staple discharge opening.

9. An apparatus adapted for positioning on a existing endoscopic surgical stapling instrument of the type having a distal end and a body portion housing a stapling mechanism having an opening at the distal end of said body portion for discharging a staple therefrom, wherein said apparatus is adapted to be positioned on the distal end of said instrument and further comprises a means for removably positioning a suture in front of and in registry with the staple discharge opening, such that a staple discharged therefrom will affix the suture to a target tissue.

10. The apparatus of claim 9, wherein the positioning means comprises a pair of complimentary suture guide grooves on the body portion adjacent the distal end, the grooves being located adjacent opposite sides of the staple discharge opening, thereby removably positioning the suture through the guide grooves and in front of and in registry with the staple discharge opening.

11. An apparatus for positioning on an existing endoscopic surgical stapling instrument of the type having a proximal end, an opposite distal end, and a body portion housing a stapling mechanism having an opening at the distal end of said body portion for discharging a staple therefrom, wherein said apparatus is adapted to be positioned on the distal end of said instrument and further comprises a means for removably positioning a suture in front of and in registry with the staple discharge opening, such that a staple discharged therefrom will affix to a target tissue, wherein the positioning means comprises a pair of complimentary suture guide holes disposed therethrough, the guide holes being located adjacent opposite sides of the staple discharge opening, thereby removably positioning the suture through the guide holes and in front of and in registry with the staple discharge opening.

12. An apparatus for positioning on an existing endoscopic surgical stapling instrument of the type having a proximal end, an opposite distal end, and a body portion housing a stapling mechanism having an opening at the distal end of said body portion for discharging a staple therefrom, wherein said apparatus is adapted to be positioned on the distal end of said instrument and further comprises a means for removably positioning a suture in front of and in registry with the staple discharge opening, such that a staple discharged therefrom will affix to a target tissue, wherein the positioning means comprises a pair of complimentary suture guide eyelets on the body portion adjacent the distal end, the eyelets being located adjacent opposite sides of the staple discharge opening, thereby removably positioning the suture through the guide eyelets in front of and in registry with the staple discharge opening.

13. A method of endoscopic suture placement at a predetermined site comprising affixing a suture to a target tissue with a staple wherein the staple and suture are delivered to the predetermined site by the same instrument.

* * * * *